United States Patent
Chambon et al.

(10) Patent No.: US 9,012,682 B2
(45) Date of Patent: Apr. 21, 2015

(54) PROCESS FOR CONVERTING CELLULOSE OR LIGNOCELLULOSIC BIOMASS USING STABLE NON-ZEOLITE SOLID LEWIS ACIDS BASED ON TIN OR ANTIMONY ALONE OR AS A MIXTURE

(75) Inventors: Flora Chambon, Bron (FR); Nadine Essayem, Saint Just Chaleyssin (FR); Franck Rataboul, Lyons (FR); Catherine Pinel, Lyons (FR); Amandine Cabiac, Givors (FR); Emmanuelle Guillon, Vourles (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 143 days.

(21) Appl. No.: 13/995,533

(22) PCT Filed: Dec. 16, 2011

(86) PCT No.: PCT/FR2011/000661
§ 371 (c)(1),
(2), (4) Date: Jun. 28, 2013

(87) PCT Pub. No.: WO2012/085361
PCT Pub. Date: Jun. 28, 2012

(65) Prior Publication Data
US 2013/0281734 A1 Oct. 24, 2013

(30) Foreign Application Priority Data

Dec. 22, 2010 (FR) ..................................... 10 05025

(51) Int. Cl.
*B01J 23/14* (2006.01)
*B01J 23/18* (2006.01)
*C07C 51/00* (2006.01)

(52) U.S. Cl.
CPC *B01J 23/14* (2013.01); *B01J 23/18* (2013.01); *C07C 51/00* (2013.01)

(58) Field of Classification Search
None
See application file for complete search history.

(56) References Cited

U.S. PATENT DOCUMENTS 6,306,364 B1 * 10/2001 Valencia et al. ............... 423/713
2013/0231497 A1 * 9/2013 Zhou et al. .................... 560/179

OTHER PUBLICATIONS

International Search Report from PCT/FR2011/000661 dated Mar. 27, 2012.
Lingzhao Kong et al. "Hydrothermal catalytic conversion of biomass for lactic acid production" Journal of Chemical Technology & Biotechnology, vol. 83, No. 3, [Mar. 1, 2008], pp. 383-388.
Martin Spangsberg Holm et al. "Conversion of Sugars to Lactic Acid Derivatives Using Heterogeneous Zeotype Catalysts" Science, AAAS, vol. 328, No. 5978, [Apr. 30, 2010], pp. 602-605.

* cited by examiner

*Primary Examiner* — Yevegeny Valenrod
(74) *Attorney, Agent, or Firm* — Millen, White, Zelano & Branigan, P.C.

(57) ABSTRACT

The invention relates to a process for transformation of lignocellulosic biomass or cellulose using stable non-zeolitic heterogeneous catalysts that are based on tin and/or antimony, preferably dispersed on a substrate. The use of these catalysts makes it possible to obtain directly lactic acid with high selectivity while limiting the production of oligosaccharides and soluble polymers.

16 Claims, No Drawings

PROCESS FOR CONVERTING CELLULOSE OR LIGNOCELLULOSIC BIOMASS USING STABLE NON-ZEOLITE SOLID LEWIS ACIDS BASED ON TIN OR ANTIMONY ALONE OR AS A MIXTURE

FIELD OF THE INVENTION

The invention relates to a process for transformation of lignocellulosic biomass or cellulose into lactic acid using stable heterogeneous catalysts that are based on tin and/or antimony, optionally dispersed on a substrate. The use of these catalysts makes it possible to obtain directly lactic acid with high selectivity while limiting the production of oligosaccharides and soluble polymers.

PRIOR ART

For several years, there has been a very sharp resurgence of interest for the incorporation of products of renewable origin within the fuel and chemistry branches, in addition to or in place of products of fossil origin. One possible method is the conversion of cellulose, contained in the lignocellulosic biomass, into chemical products or intermediate products, such as lactic acid.

The term lignocellulosic biomass (BLC) or lignocellulose encompasses several products that are present in variable quantities according to the origin thereof: cellulose, hemicellulose and lignin. Hemicellulose and cellulose constitute the carbohydrate portion of lignocellulose. These are polymers of sugars (pentoses and hexoses). Lignin is a macromolecule that is rich in phenolic units. Lignocellulosic biomass is defined as, for example, the products that are obtained from forestry operations and the sub-products that are obtained from agriculture, such as straw as well as certain dedicated plants with a high agricultural yield.

The production of chemical products from lignocellulosic biomass makes it possible both to reduce the energy dependency relative to petroleum and to protect the environment through the reduction of greenhouse gas emissions without using resources designed for food uses.

The direct transformation of lignocellulosic biomass or cellulose into chemical products or intermediate products, such as lactic acid, is a particularly advantageous method. Direct transformation is defined as the cellulose-lactic acid transformation without isolating the glucose intermediate product.

Lactic acid is a carboxylic acid, its chemical formula is $C_3H_6O_3$, and its structure is reflected in its systematic name, 2-hydroxy-propanoic acid. Since it has an asymmetric carbon, two enantiomers of lactic acid exist. The applications of lactic acid are primarily those of its polymer PLA (polylactic acid) as a food preservative but also as biodegradable polymers, pesticides and herbicides.

The production of lactic acid can be done by a chemical method or by a biological method. The chemical methods for the production of lactic acid that are known to one skilled in the art are carried out via the transformation of petrochemical intermediate products such as the hydrolysis of lactonitrile or the hydration of propionic acid. Lactic acid can also be produced by fermenting polysaccharides, which can be obtained from the biomass, for example obtained from grains such as wheat or corn. The patent application EPA-1 953 234 relates to a process for the production of lactic acid by fermenting a sugar cane extract, by means of the microorganism that belongs to the genera *Bacillus* or *Sporolactobacillus*.

The upgrading of the lignocellulosic biomass or the cellulose that is contained in the biomass by heterogeneous catalysis is described in the literature. For example, the hydrolysis of the cellulose into glucose or into sorbitol in an aqueous medium with heterogeneous metallic catalysts is described in the patent application EP-A-2 011 569. Rinaldi et al. describe the depolymerization of cellulose in an ionic liquid medium in the presence of Brønsted acid catalysts (Angew. [Applied] Chem. Int. Ed., 2008, 47, 8047-8050). Zeng et al. describe the conversion of glucose into lactic acid, 5-hydroxy methylfurfural and levulinic acid in the presence of basic catalysts of Al/Zr mixed oxide types (Catal. Lett. (2009) 133: 221-226). Holm et al. describe the use of zeolitic Lewis acid heterogeneous catalysts for transforming glucose or fructose into lactic acid (Science (2010), 328, 602-605). The Lewis acid zeolitic catalyst is, for example, the Sn-beta zeolite or the Ti-beta zeolite.

Also, the production of lactic acid by treatment of cellulose/lignocellulose under hydrothermal conditions in the presence of basic homogeneous catalysts is known. By basic homogeneous catalysis, Fangmin Jin and Heiji Einomoto (J. Mater. Sci. (2008) 43: 2463-2471) report a yield of 27% of lactic acid in the presence of $Ca(OH)_2$ at a temperature of 300° C. in less than 5 minutes of reaction. Kong et al. (J. Chem. Technol. Biotechnol. 83: 383-388 (2008)) describe a hydrothermal process for the production of lactic acid from biomass in a subcritical water medium in the presence of cations of transition metals Zn(II), Ni(II), Co(II) and Cr(III). The patent application WO 03/035582 describes the hydrogenolysis of sorbitol at 200° C. by using (Ni,Re)/C catalysts that leads to lactic acid yields of 5% and 30% of diols (ethylene glycol and propylene glycol). Shimizu et al. (Green Chem. 2009, 11, 1627-1632) demonstrated the essential role of Brønsted acidity on the hydrolysis of cellulose into glucose. Zhang et al. (Angew. Chem. Int. Ed. 2008, 47, 8510-8513) studied the transformation of cellulose into ethylene glycol and propylene glycol on activated carbon/tungsten carbide catalysts with nickel as a promoter (T=245° C., P=6 MPa, $H_2$, water).

There is no process that allows a direct transformation—i.e., without isolating the glucose intermediate product—of cellulose or, more broadly, lignocellulosic biomass into lactic acid by means of heterogeneous catalysts. The applicant discovered a process for direct transformation of cellulose, present in the lignocellulosic biomass, into lactic acid, using stable non-zeolitic heterogeneous catalysts that are based on tin or antimony by itself or in a mixture, optionally dispersed on a substrate. This process makes it possible to obtain a high yield of lactic acid.

SUMMARY OF THE INVENTION

The invention consists of a process for transformation of lignocellulosic biomass or cellulose into lactic acid in the presence of water, using a stable non-zeolitic heterogeneous catalyst that is based on tin and/or antimony, preferably dispersed on an oxide-based substrate or a carbon-containing substrate.

DETAILED DESCRIPTION OF THE INVENTION

The process for transformation of the cellulosic biomass or cellulose according to this invention comprises bringing said biomass or cellulose into contact, in the presence of water, with a non-zeolitic heterogeneous catalyst that is based on tin and/or antimony, with said catalyst having Lewis-type acid sites.

Said non-zeolitic heterogeneous catalyst is preferably based on tin oxide and/or antimony oxide.

In a preferred way, said catalyst is dispersed on a substrate that is based on at least one oxide or a carbon-containing substrate.

The process makes it possible to obtain high conversions of the reagent and important selectivities, in particular high yields of lactic acid, while limiting the formation of oligosaccharides or water-soluble polymers. These conversions and selectivities are obtained only under hydrothermal conditions (presence of water) and in the presence of stable non-zeolitic catalysts that are based on tin and/or antimony having Lewis-type acid properties. Actually, the solid catalysts for the most part having a Brønsted acidity promote the production of soluble oligosaccharides and/or soluble polymers, exhibiting a lower selectivity in desired chemical intermediate products. The heterogeneous catalysts that are based on tin and/or antimony, preferably dispersed on a substrate that is based on at least one oxide or a carbon-containing substrate, are stable in the reaction medium.

In a preferred way, the oxide-based substrates are selected from among the oxide(s) of aluminum and/or zirconium and/or titanium and/or niobium.

The non-zeolitic catalyst that is based on tin and/or antimony, preferably dispersed on said substrate, has Lewis-type acid sites. The content of Lewis-type acid sites of the catalyst is preferably greater than 50% of the total content of acid sites. The term total content of acid sites is defined as meaning the sum of the Lewis acid sites and the Bronsted acid sites.

The Feedstock

The lignocellulosic biomass essentially consists of three natural components that are present in variable amounts according to the origin thereof: cellulose, hemicellulose, and lignin.

The cellulose $(C_6H_{10}O_5)_n$ represents the major portion (50-60%) of the composition of the lignocellulosic biomass. The cellulose is a semi-crystalline linear homopolymer of glucose connected by β bonds. The cellulose is insoluble in water at ambient temperature and pressure.

Hemicellulose is the carbohydrate that is second in quantity after cellulose and constitutes 20 to 40% by weight of the lignocellulosic biomass. In contrast to cellulose, this polymer consists for the most part of monomers of pentoses (cyclic compounds with five atoms) and hexoses (cyclic compounds with 6 atoms). Hemicellulose is an amorphous heteropolymer with a degree of polymerization that is less than that of cellulose (30-100) and that is generally water-soluble.

Lignin is an amorphous macromolecule that is present in the lignocellulosic compounds in variable proportions according to the origin of the material (straw ~15%, wood: 20-26%). Its function is mechanical reinforcement, hydrophobization, and support of plants. This macromolecule that is rich in phenolic units can be described as a resultant of the combination of three monomer units of the propyl-methoxy-phenol type. Its molar mass varies from 5,000 g/mol to 10,000 g/mol for hardwoods and reaches 20,000 g/mol for softwoods.

The lignocellulosic raw material can consist of wood or plant waste. Other nonlimiting examples of lignocellulosic biomass material are waste from agricultural operations (straw, grasses, stems, pits, shells, . . . ), waste from forestry operations (initial cutting products, bark, sawdust, chips, scraps, . . . ), products from forestry operations, dedicated crops (short-rotation shrubs), waste from the food-processing industry (waste from the industry of cotton, bamboo, sisal, banana, corn, switchgrass, alfalfa, coconut, bagasse, . . . ), household organic waste, waste from wood transformation plants, scrap wood from construction, and paper, which may or may not be recycled.

The feedstock that is used in the process according to the invention is lignocellulosic biomass or cellulose. The cellulose that is used may be crystalline, partially amorphous, or amorphous.

The lignocellulosic biomass feedstock can be used in its raw form, i.e., in its entirety, i.e., containing its three components: cellulose, hemicellulose and lignin. The raw biomass generally comes in the form of fibrous residues or powder. In general, it is ground (shredded) to allow its transport.

The lignocellulosic biomass feedstock can also be used in its pretreated form, i.e., in a form that contains at least one cellulosic portion after extraction of lignin and/or hemicellulose.

The biomass preferably undergoes a pretreatment so as to increase the reactivity and the accessibility of cellulose within the biomass before its transformation. These pretreatments are of a mechanical, thermochemical, thermo-mechanical-chemical and/or biochemical nature and bring about the partial or total decrystallization of cellulose, the total or partial solubilization of hemicellulose and/or lignin, or the partial hydrolysis of hemicellulose following the treatment.

The mechanical treatments go beyond simple shredding because they modify the chemical structure of the components. They improve the accessibility and the reactivity of cellulose by its partial or total decrystallization and by the increase in the exchange surface area. The mechanical treatments include the reduction of the size of fibers or elementary particles, for example by chipping the biomass with a cutter, by grinding the biomass (adjustment of the grain size), destructuring chips on a press, or defibration by chip abrasion, after preheating. The mechanical treatments can be performed in decentralized mode close to where the biomass is produced or in centralized mode that directly feeds the transformation.

The thermochemical treatments include the baking of the biomass at high temperature (150-170° C.) in a dilute acid medium (primarily sulfuric acid, but also phosphoric acid, acetic acid, or formic acid), in an alkaline medium (soda, sulfites, lime, . . . ) or in an oxidizing medium (wet oxidation with air or oxygen; peroxide in an alkaline medium; peracetic acid). The other thermochemical treatments include treatments with solvents (hot ethanol) or roasting that can be defined as pyrolysis at moderate temperature and with a controlled dwell time because it is accompanied by partial destruction of the lignocellulosic material. The known technologies for roasting are, for example, the rotary kiln, the moving bed, the fluidized bed, the heated endless screw, and the contact with metal balls that provide heat. These technologies can optionally use a gas that circulates in co-current or counter-current such as nitrogen or any other inert gas under the conditions of the reaction.

The thermo-mechanical-chemical treatments include vapor treatments (vapor explosion also called flash hydrolysis or "steam explosion"), the AFEX (ammonia fiber explosion) treatment with ammonia, or two-screw extrusion with various chemical reagents.

The pretreatment makes it possible to prepare the lignocellulosic biomass by separating the carbohydrate portion of the lignin and by adjusting the size of the biomass particles that are to be treated. The size of the biomass particles after pretreatment is generally less than 5 mm, preferably less than 500 microns.

The Catalyst

The catalysts that are used for the transformation of the lignocellulosic biomass or cellulose are based on tin and/or antimony, preferably dispersed on the surface of a substrate, preferably a substrate that is based on oxides selected from among the oxide(s) of aluminum and/or zirconium and/or titanium and/or niobium or a carbon-containing substrate, whereby said catalysts have Lewis-type acid sites.

The acidity of a catalyst is the resultant of two combined types of acidity: Lewis acidity, characterized by the presence of an electron gap on an atom, and Brønsted acidity, characterized by a capability of giving up a proton. The nature of the acid sites can be characterized by adsorption of pyridine followed by IR spectroscopy in accordance with the method that is described in [M. Guisnet, P. Ayrault, C. Coutanceau, M. F. Alvarez, J. Datka, *J. Chem. Soc., Faraday Trans.* 93, 1661 (1997)].

The solids according to the invention are characterized by superficial acidic properties that are for the most part of the Lewis acid type; preferably, the content of Lewis acid sites is greater than 50% of the total content of acid sites. The Lewis-type acid sites are associated with the presence of tin and/or antimony radicals that are coordinatively unsaturated but also with radicals that are characteristic of the substrate, such as, for example, in the case of an oxide-based substrate: $Al^{3+}$, $Zr^{4+}$, $Ti^{4+}$, and $Nb^{5+}$. It is known that the coordination of the tin and/or antimony radicals depends on their dispersion, the Sn or Sb content, the nature of the precursors, and the heat treatments. The Lewis acidity may be characterized by, for example, IR spectroscopy.

When the substrate that is used for dispersing tin and/or antimony is an oxide, it comprises at least one oxide, preferably selected from among alumina, zirconia, niobium oxide, titanium oxide, silica, alumino-phosphates, or mesostructured compounds, by themselves or in a mixture, prepared according to any technique that is known to one skilled in the art. For example, the substrates can be synthesized by precipitation, or sol-gel synthesis followed by a heat treatment. The solids that are obtained have the advantage of being mesoporous and stable, thermally and under hydrothermal conditions.

The substrate can also be a carbon-containing substrate such as, for example, activated carbons, carbon black, carbon-containing microporous or mesoporous solids, such as, for example, carbon nanotubes, or carbon fibers. The carbon-containing substrates are prepared according to any technique that is known to one skilled in the art. The carbon-containing substrates can undergo a treatment so as to modify, for example, their properties of acidity, hydrophobicity, and texture. For example, the heat treatments, oxidizing treatments and reducing treatments can be cited.

In a preferred manner, the substrates are based on oxide(s).

The tin and/or antimony content is between 1 to 100% by weight, preferably between 1 and 50% by weight, preferably between 1 and 30%, and even more preferably between 1 and 20% by weight, with the percentages being expressed in terms of % by weight of metal relative to the total mass of catalyst.

The precursors of tin or antimony are selected from among hydrides, halides, oxides, sulfides, or organometallic compounds respectively of tin or antimony.

For example, tin hydrides, tin halides (chlorides, bromides, iodides, fluorides of tin), tin oxides, and tin sulfides will be cited. The tin chlorides are the usual precursors. The use of tin chloride in solution in hydrochloric acid is preferred. The tin precursors can be organometallic compounds like, for example, the alkyl tin compounds such as tetrabutyltin.

For the antimony precursors, antimony hydrides, antimony halides (chlorides, iodides and fluorides of antimony), antimony oxides, and antimony sulfides will be cited. The antimony precursors can also be organometallic compounds of antimony.

The preparation of stable heterogeneous catalysts that are based on tin or antimony by itself or in a mixture, preferably dispersed on the oxide-based substrate or the carbon-containing substrate, is carried out by any method that is known to one skilled in the art.

One method of preparation consists in an impregnation of a solution of stannic acid and/or antimony oxide and zirconium hydroxide and/or titanium hydroxide and/or aluminum hydroxide and/or niobium hydroxide, optionally followed by drying.

The presence of tin and/or antimony on the oxide-based substrate brings about the formation of tin oxide and/or antimony oxide.

The catalyst that is used in this invention and that is based on tin and/or antimony, preferably dispersed on a substrate that is based on oxides selected from among the oxide(s) of aluminum and/or zirconium and/or titanium and/or niobium or on a carbon-containing substrate can undergo a heat treatment at the end of its preparation or during its preparation. Said heat treatment is advantageously carried out between 300° C. and 1,000° C. It can be carried out in air, under a reducing atmosphere, such as hydrogen, or under nitrogen, pure or in a mixture.

Said heat treatment of the catalyst can be carried out at any stage of its preparation, before or after the shaping stage.

The thus obtained catalyst is stable, thermally and under hydrothermal conditions.

The catalyst that is used in this invention can contain a binder.

The catalyst that is used in this invention can be in the form of powder, extrudates, balls, or pellets.

The catalyst that is used according to the invention is stable and can be regenerated, i.e., it does not undergo lixiviation during the reaction. At the end of a stage for washing or combustion of the hydrocarbon radicals that are deposited on the catalyst after reaction, the catalyst has the same initial catalytic performances.

Transformation Process

The process for transformation of the lignocellulosic biomass or cellulose according to the invention comprises the reaction in a water-containing medium in the presence of the catalytic composition according to the invention.

Water-containing medium refers to the conventional liquid media like alcohols, such as methanol or ethanol, and water, and the non-conventional media like the ionic liquids or the supercritical media of liquid-type density.

The content by mass of water in the medium is generally greater than 1%. The medium can also consist entirely of water. Preferably, the medium is water.

This process can be carried out in the presence of a gas that is selected from among air, a neutral gas ($N_2$, He, Ar . . . ) or a reducing gas like hydrogen.

The process is performed at temperatures of between 160° C. and 250° C., preferably between 175 and 250° C., and at a pressure of between 0.5 and 20 MPa, preferably between 2 and 10 MPa.

The reaction can be performed according to different embodiments. Thus, the reaction can be implemented intermittently or continuously, for example in a fixed bed. It is possible to perform the reaction in a closed or semi-open reactor.

The catalyst is introduced into the process at a rate of a quantity corresponding to a biomass/catalyst mass ratio of between 1 and 1,000, preferably between 1 and 500, preferably between 1 and 100, preferably between 1 and 50, and even preferably between 1 and 25.

The biomass is introduced into the process at a rate of a quantity that corresponds to a (water-containing medium)/biomass mass ratio of between 1 and 1,000, preferably between 1 and 500, and even preferably between 5 and 100. The dilution rate of the biomass in the aqueous medium is therefore between 1:1 and 1:1,000, preferably between 1:1 and 1:500, and even preferably between 1:5 and 1:100.

If a continuous process is selected, the mass speed per hour (mass feedstock/catalyst mass flow rate) is between 0.01 and 5 $h^{-1}$, preferably between 0.02 and 2 $h^{-1}$.

The Products that are Obtained and their Mode of Analysis

After the reaction, the reaction medium is sampled and centrifuged. The reaction liquid is next analyzed by high performance liquid chromatography (HPLC) by using refractometry for determining the content of conversion products of the aqueous solution.

The products of the reaction are water-soluble. They consist of monosaccharides and their derivatives, oligosaccharides, but also soluble polymers that are formed by successive combinations of the derivatives of monosaccharides.

Monosaccharides refer to the simple sugars (hexoses, pentoses) that are produced by complete depolymerization of cellulose and/or hemicellulose, in particular glucose, mannose, xylose, fructose, . . . .

Monosaccharide derivatives refer to the products that can be obtained by dehydration, isomerization, reduction or oxidation:
- Alcohol sugars, alcohols and polyols: in particular sorbitol, xylitol, glycerol, ethylene glycol, propylene glycol, ethanol, methylbutane diol, . . . ,
- Ketones, hexane-diones such as 2,5-hexanedione, . . . ,
- Carboxylic acids and their esters, lactones: formic acid, levulinic acid, alkyl levulinates, lactic acid, alkyl lactates, glutaric acid, alkyl glutarates, 3-hydroxypropanoic acid, 3-hydroxybutyrolactone, γ-butyrolactone,
- Cyclic ethers, such as tetrahydrofuran (THF), methyl tetrahydrofuran (Me-THF), dicarboxylic acid furan, 5-(hydroxymethyl)furfural.

Oligosaccharides refer to a carbohydrate that has as its composition $(C_6H_{10}O_5)_n$, where n is greater than 1, obtained by partial hydrolysis of cellulose, or hemicellulose, or starch.

Soluble polymers refer to all of the products that are obtained from condensation between monosaccharides, oligosaccharides and/or derivatives of monosaccharides.

The quantity of water-soluble reaction products (monosaccharides and derivatives, oligosaccharides, soluble polymers) is determined by the COT [TOC] (Total Organic Carbon) analysis that consists of the measurement of carbon in solution. The quantity of monosaccharides and their derivatives is determined by HPLC analyses.

The conversion (equivalent to % of solubilization) of the biomass or cellulose is calculated according to the following equation:

$$C=100*C_{solubilized}/C_{initial}$$

in which $C_{solubilized}$ represents the quantity of solubilized carbon that is analyzed by TOC (mg), and $C_{initial}$ represents the quantity of carbon at the beginning of the reaction that is contained in the biomass or solid cellulose.

The molar yields of glucose derivatives are calculated by means of HPLC analysis. Each compound is corrected by the carbon atom number contained in the glucose unit.

The molar yields of a derivative i are calculated as follows:

$$Rdt_i=100*(nC_{Pi}/6)*(P_i/Glu_o)$$

where $nC_{Pi}$ represents the number of carbon atoms of the derivative i, Pi represents the number of moles of the product $P_i$, and $Glu_o$ represents the number of moles of glucose units contained in the biomass or cellulose at the beginning of the reaction.

The formation of oligosaccharides and soluble polymers corresponds to a loss of carbon. This loss of carbon is deduced from TOC and HPLC analyses. The yield of oligosaccharides and soluble polymers is calculated according to the following equation:

$$Rdt_{olig}=C-\Sigma rdt_i$$

where C represents the conversion of the cellulose and $\Sigma rdt_i$ represents the sum of molar yields of all of the monosaccharides and their derivatives that are analyzed by HPLC.

EXAMPLES

Example 1

Preparation of Non-Zeolitic Catalyst C1 that is Based on Tin Oxide, Dispersed on a Substrate that is Based on Alumina Oxide (in Accordance with the Invention)

The catalyst is prepared by using aluminum hydroxide and pentahydrated tin chloride as raw material. 5.0 g of aluminum hydroxide is subjected to impregnation with nascent humidity with an aqueous solution of tin chloride (3.0 g of $SnCl_4$, $5H_2O$ in 4.5 g of water). The solid that is obtained is then dried at 80° C. for 24 hours.

Next, the solid is calcined under a flow of dry air at the temperature of 700° C. for 3 hours. At the end of these treatments, the tin oxide that is deposited on alumina and the substrate contains 15% by weight of tin. The catalyst that is obtained is mesoporous.

The proportion of Lewis acid sites of the catalyst C1 is greater than 90%.

Example 2

Preparation of an Sn-Beta Zeolitic Catalyst C2 (not in Accordance with the Invention)

The catalyst C2 is prepared according to the teaching of the U.S. Pat. No. 5,968,473. A gel of molar composition: $SiO_2$: 1/120 $SnO_2$:0.54 TEAOH: 7.5 $H_2O$: 0.54 HF is prepared by hydrolysis of tetraethyl orthosilicate or TEOS (98%, Merck) in an aqueous solution of tetraethylammonium hydroxide or TEAOH (35%, Aldrich). Next, a solution of $SnCl_4$, $5H_2O$ (98%, Aldrich) is added. The mixture is stirred until the ethanol that is formed during the hydrolysis of TEOS is completely evaporated. Next, hydrofluoric acid HF is added (48%). Dealuminified beta zeolite seeds are thus obtained. The crystallization is carried out in a Teflon-coated stirred autoclave at 140° C. The autoclave is then cooled. The solid is recovered by filtering, washed thoroughly with distilled water. After drying at 100° C., the solid is calcined at 580° C. The solid is characterized by X-ray diffraction: Sn-beta zeolite is readily obtained. The catalyst C2 is microporous.

Example 3

Transformation of Cellulose that Uses the Catalysts that are Obtained According to Examples 1 and 2

This example relates to the conversion of cellulose that uses the catalysts C1 and C2 for the production of lactic acid.

65 ml of water, 1.6 g of Avicel® cellulose (70% crystallinity), and 0.68 g of catalyst of Examples 1 and 2 are introduced into a 100 ml autoclave. It is heated to 190° C., and 5 MPa of $H_2$ is injected. The total pressure then reaches 6 MPa. After 24 hours of reaction, the reaction medium is sampled and centrifuged. The reaction liquid is next analyzed by high-pressure liquid chromatography (HPLC) by using refractometry for determining the content of conversion products of the aqueous solution according to the equations described above.

The transformation reaction was also carried out with $Al_2O_3$ oxide substrates.

The results that are obtained are referenced in Table 1.

TABLE 1

Conversion of Cellulose and Yields of Lactic Acid and Oligosaccharides and Soluble Polymers Using Different Catalysts.

| Catalyst | Cellulose Conversion (%) | Molar Yield of Lactic Acid (%) | Molar Yields of Oligosaccharides and Soluble Polymers (%) |
|---|---|---|---|
| $Al_2O_3$ (Anomalous) | 35 | 3 | 7 |
| AlSn (C1) | 44 | 23 | 0 |
| Sn-Beta (C2, Anomalous) | 27 | 10 | 6 |

For the catalyst $Al_2O_3$, not in accordance with the invention, it is found that the quantity of lactic acid that is formed represents 3 mol % of the quantity of initial cellulose, with 7 mol % of oligosaccharides and soluble polymers. The cellulose conversion is 35%.

Thus, for the catalyst AlSn, it is found that the quantity of lactic acid that is formed represents 23 mol % of the quantity of initial cellulose, without formation of oligosaccharides and soluble polymers. The conversion is 44%.

The use of Sn-beta zeolitic Lewis acid catalysts leads to the less important formation of formed lactic acid. The quantity of lactic acid product that is formed represents 10 mol % of the quantity of initial cellulose. A formation of 6% oligosaccharides and soluble polymers is noted. The conversion is 27%.

After 24 hours of reaction, the analysis of the reaction medium shows that the catalyst C1 is stable under the conditions of the reaction. Actually, the loss in tin is less than 0.1%. After 24 hours of reaction, the catalyst C2, not in accordance with the invention, has a silicon loss of 10% by weight and a tin loss of 0.3% by weight.

Thus, these examples demonstrate the production of lactic acid with high yield by direct transformation of cellulose via Sn Lewis-acid-based heterogeneous mesoporous catalysts that have stable oxide substrates while limiting the formation of oligosaccharides and soluble polymers.

The invention claimed is:

1. Process for transformation of cellulosic biomass or cellulose into lactic acid, comprising bringing said biomass or cellulose into contact, in the presence of water, with a non-zeolitic heterogeneous catalyst that is based on tin and/or antimony, whereby said catalyst has Lewis-type acid sites.

2. Process according to claim 1, in which said catalyst is based on tin oxide and/or antimony oxide.

3. Process according to claim 1, in which said catalyst is dispersed on a substrate that is based on at least one oxide or a carbon-containing substrate.

4. Process according to claim 3, in which said oxide-based substrate is selected from among the oxides of aluminum and/or zirconium and/or titanium and/or niobium.

5. Process according to claim 3, in which the carbon-containing substrate is selected from among activated carbons, carbon black, and carbon-containing microporous or mesoporous solids such as carbon nanotubes, or carbon fibers.

6. Process according to claim 1, in which the content of Lewis-type acid sites is greater than 50% of the total content of acid sites.

7. Process according to claim 1, in which the content of tin and/or antimony is between 1 and 100% by weight, preferably between 1 and 50%, preferably between 1 and 30% by weight, and even more preferably between 1 and 20% by weight relative to the total mass of the catalyst.

8. Process according to claim 1, in which the precursors of tin or antimony are selected from among hydrides, halides, oxides, sulfides, or organometallic compounds respectively of tin or antimony.

9. Process according to claim 1, in which the catalyst is prepared by impregnation of a solution of stannic acid and/or antimony oxide and zirconium hydroxide and/or titanium hydroxide and/or aluminum hydroxide and/or niobium hydroxide, optionally followed by drying.

10. Process according to claim 1, in which during its preparation or at the end of its preparation, the catalyst undergoes a heat treatment of between 300° C. and 1000° C., in air, under a reducing atmosphere, or in nitrogen, pure or in a mixture.

11. Process according to claim 1, in which the transformation is implemented in a water-containing medium, with said medium being selected from among the group that is formed by a liquid medium, such as alcohols or water, an ionic liquid, and a supercritical medium of liquid-type density.

12. Process according to claim 1, in which the transformation is performed at temperatures of between 160 and 250° C., preferably between 175 and 250° C., and at a pressure of between 0.5 and 20 MPa, preferably between 2 and 10 MPa.

13. Process according to claim 1, in which the catalyst is introduced with a biomass/catalyst mass ratio of between 1 and 1,000, preferably between 1 and 500, very preferably between 1 and 50, and even more preferably between 1 and 25.

14. Process according to claim 1, in which the dilution rate of the biomass in the aqueous medium is therefore between 1:1 and 1:1000, preferably between 1:1 and 1:500, and even preferably between 1:5 and 1:100.

15. Process according to claim 1, in which the reaction is implemented intermittently or continuously in a closed or semi-open reactor.

16. Process according to claim 1, characterized in that it is implemented continuously with a mass speed per hour of between 0.01 and 5 $h^{-1}$, preferably between 0.02 and 2 $h^{-1}$.

* * * * *